(12) United States Patent
Miller et al.

(10) Patent No.: US 6,495,560 B1
(45) Date of Patent: Dec. 17, 2002

(54) VITRONECTIN RECEPTOR ANTAGONIST

(75) Inventors: William H. Miller, Collegeville, PA (US); Peter J. Manley, Harleysville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/857,316

(22) PCT Filed: Dec. 3, 1999

(86) PCT No.: PCT/US99/28662

§ 371 (c)(1), (2), (4) Date: Jul. 12, 2001

(87) PCT Pub. No.: WO00/33838

PCT Pub. Date: Jun. 15, 2000

Related U.S. Application Data

(60) Provisional application No. 60/110,903, filed on Dec. 4, 1998.

(51) Int. Cl.[7] ............... A61K 31/435; C07D 471/04
(52) U.S. Cl. ............... 514/300; 514/283; 546/122
(58) Field of Search ............... 546/122; 514/300

(56) References Cited

U.S. PATENT DOCUMENTS 5,599,936 A    2/1997   Barreau et al.

FOREIGN PATENT DOCUMENTS

| WO | WO 97/01540 | 1/1997 |
| WO | WO 98/15278 | 4/1998 |
| WO | WO 98/45255 | 10/1998 |

*Primary Examiner*—Bernard Dentz
(74) *Attorney, Agent, or Firm*—Mary E. McCarthy; Stephen Venetianer; Charles M. Kinzig

(57) ABSTRACT

A compound of the formula (I) is disclosed which is a vitronectin receptor antagonist and is useful in the treatment of osteoporosis:

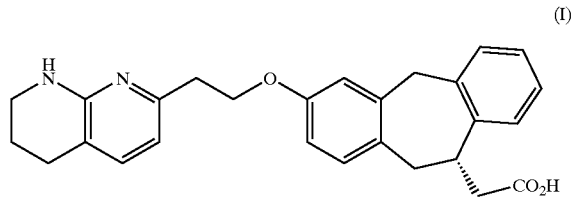

(I)

or a pharmaceutically acceptable salt thereof.

17 Claims, No Drawings

VITRONECTIN RECEPTOR ANTAGONIST

This application is a 371 of PCT/US99/28662 filed Dec. 03, 1999 which claims the benefit of No. 60/110,903 filed Dec. 04, 1998.

FIELD OF THE INVENTION

This invention relates to a pharmaceutically active compound which inhibits the vitronectin receptor and is useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et al., *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al., *J. Biol. Chem.*, 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.*, 1994, 28, 1815. Additionally, Brooks, et al., *Cell,* 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol.*, 1990, 71, 741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.*, 1993, 51, 206), and its role in angiogenesis has been confirmed. Brooks, et al., *Science,* 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 discloses that echistatin, a snake venom peptide which contains the RGD sequence, is a potent inhibitor of bone resorption in tissue culture, and inhibits attachment of osteoclasts to bone.

It has now been discovered that a certain compound is a potent inhibitor of the $\alpha_v\beta_3$ and $\alpha_v\beta_5$ receptors. In particular, it has been discovered that such compound is more potent inhibitors of the vitronectin receptor than the fibrinogen receptor.

SUMMARY OF THE INVENTION

This invention comprises a compound of the formula (I) as described hereinafter, which has pharmacological activity for the inhibition of the vitronection receptor and is useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I) and a pharmaceutically carrier.

This invention is also a method of treating diseases which are mediated by the vitronectin receptor. In a particular aspect, the compound of this invention is useful for treating atherosclerosis, restenosis, inflammation, cancer and diseases wherein bone resorption is a factor, such as osteoporosis.

DETAILED DESCRIPTION

This invention comprises a novel compound which is a more potent inhibitor of the vitronectin receptor than the fibrinogen receptor. The novel compound comprises a dibenzocycloheptene core in which a nitrogen-containing substituent is present on one of the aromatic six-membered rings of the dibenzocycloheptene and an aliphatic substituent containing an acidic moiety is present on the seven-membered ring of the dibenzocycloheptene. The dibenzocycloheptene ring system is believed to orient the substituent sidechains on the six and seven membered rings so that they may interact favorably with the vitronectin receptor. It is preferred that about twelve to fourteen intervening covalent bonds via the shortest intramolecular path will exist between the acidic group on the aliphatic substituent of the seven-membered ring of the dibenzocycloheptene and the nitrogen of the nitrogen-containing substituent on one of the aromatic six-membered ring of the dibenzocycloheptene.

This invention comprises a compound of formula (I):

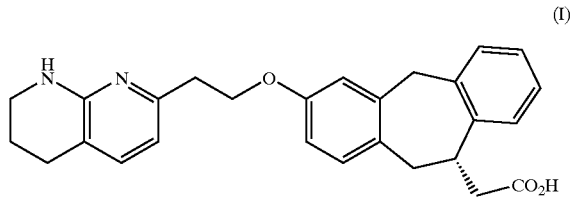

(I)

or a pharmaceutically acceptable salt thereof.

The compound of formula (I) inhibits the binding of vitronectin and other RGD-containing peptides to the vitronectin receptor. Inhibition of the vitronectin receptor on osteoclasts inhibits osteoclastic bone resorption and is useful in the treatment of diseases wherein bone resorption is associated with pathology, such as osteoporosis and osteoarthritis.

In another aspect, this invention is a method for stimulating bone formation which comprises administering a compound of formula (I) which causes an increase in osteocalcin release. Increased bone production is a clear benefit in disease states wherein there is a deficiency of mineralized bone mass or remodeling of bone is desired, such as fracture healing and the prevention of bone fractures.

Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behcet's disease, osteomalacia, hyperostosis and osteopetrosis, could benefit from administering a compound of this invention.

Additionally, since the compound of the instant invention inhibits vitronectin receptors on a number of different types of cells, said compound would be useful in the treatment of inflammatory disorders, such as rheumatoid arthritis and psoriasis, and cardiovascular diseases, such as atherosclerosis and restenosis. The compound of Formula (I) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compound of the present invention may also be useful for wound healing.

The compound of the present invention is also useful for the treatment, including prevention, of angiogenic disorders. The term angiogenic disorders as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compound of the present invention inhibit tumor tissue angiogenesis, thereby preventing tumor metastasis and tumor growth.

Thus, according to the methods of the present invention, the inhibition of angiogenesis using the compound of the present invention can ameliorate the symptoms of the disease, and, in some cases, can cure the disease.

Another therapeutic target for the compound of the instant invention is eye diseases chacterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of formula (I) and an antineoplastic agent, such as topotecan and cisplatin.

The novel compound of this invention is (S)-10,11-dihydro-3-[2-(5,6,7,8-tetrahydro-1,8-naphthyridin-2-yl)-1-ethoxy]-5H-dibenzo[a,d]cycloheptene-10-acetic acid or a pharmaceutically acceptable salt thereof.

According to the present invention, the (S) configuration of the formula (I) compound is preferred.

Also included in this invention are prodrugs of the compound of this invention. Prodrugs are considered to be any covalently bonded carriers which release the active parent drug according to formula (I) in vivo. Thus, in another aspect of this invention are novel prodrugs, which are also intermediates in the preparation of the formula (I) compound, of formula (II):

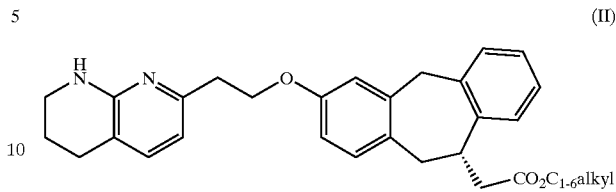

(II)

or a pharmaceutically acceptable salt thereof.

Abbreviations and symbols commonly used in the peptide and chemical arts are used herein to describe the compound of this invention. In general, the amino acid abbreviations follow the IUPAC-IUB Joint Commission on Biochemical Nomenclature as described in Eur. J. Biochem., 158, 9 (1984).

$C_{1-6}$alkyl as applied herein means an optionally substituted alkyl group of 1 to 6 carbon atoms, and includes methyl, ethyl, n-propyl, isopropyl, n-butyl, isobutyl, t-butyl, pentyl, n-pentyl, isopentyl, neopentyl and hexyl and the simple aliphatic isomers thereof.

Any $C_{1-6}$ alkyl may be optionally substituted with the group $R^x$, which may be on any carbon atom that results in a stable structure and is available by conventional synthetic techniques. Suitable groups for $R^x$ are $C_{1-4}$alkyl, OR", SR", $C_{1-4}$alkylsulfonyl, $C_{1-4}$alkylsulfoxyl, —CN, N(R")$_2$, CH$_2$N(R")$_2$, —NO$_2$, —CF$_3$, —CO$_2$R", —CON(R")$_2$, —COR", —NR"C(O)R", F, Cl, Br, I, or CF$_3$S(O)$_r$—, wherein r is 0, 1 or 2 and R" is H or $C_{1-6}$alkyl.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THP refers to tetrahydrofuiran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

Compound of the formula (I) may be prepared by the methods described in Bondinell et al., PCT Publication No. WO 97/01540 (International Application No. PCT/US96/11108), published Jan. 16, 1997, the entire disclosure of which is incorporated herein by reference.

Additionally, the compound of formula (I) is prepared by methods analogous to those described in the schemes that are detailed hereinafter.

Scheme I

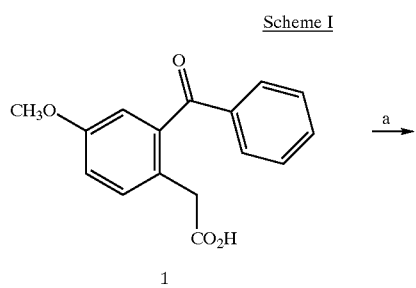

1

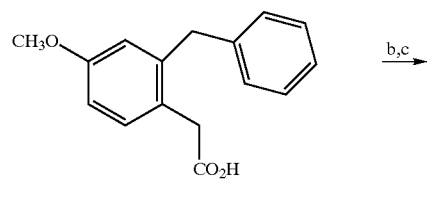

2

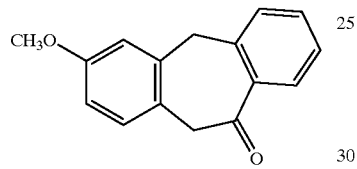

3 a) 10% Pd/C, HOAc; b) SOCl$_2$, toluene; c) AlCl$_3$, CH$_2$Cl$_2$

Scheme I details the preparation of an intermediate useful in the preparation of formula (I) compound.

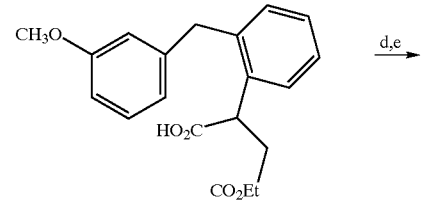

4

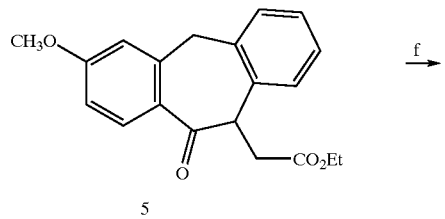

5

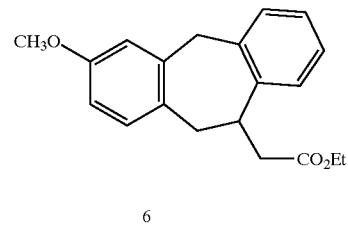

6 a) LiN(TMS)$_2$, ethyl bromoacetate; b) Jones reagent, OsO$_4$; c) H$_2$, 10% Pd/C, HOAC; d) C$_2$O$_2$Cl$_2$, DMF; e) AlCl$_3$, CH$_2$Cl$_2$, RT; f) H$_2$, 10% Pd/C, HOAC Scheme II also details the preparation of an intermediate useful in the preparation of formula (I) compound.

Scheme II

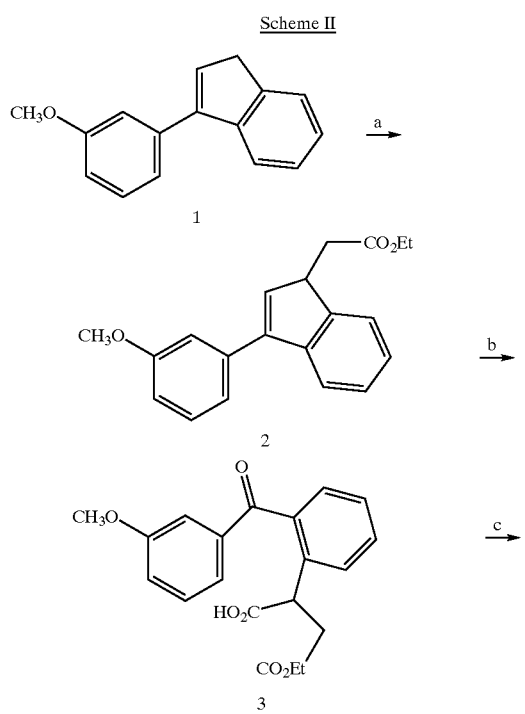

Scheme III

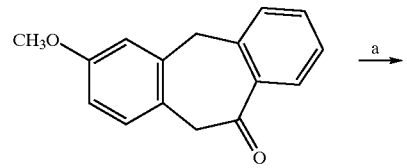

1

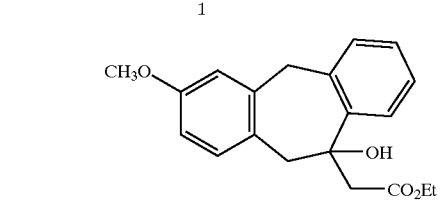

2

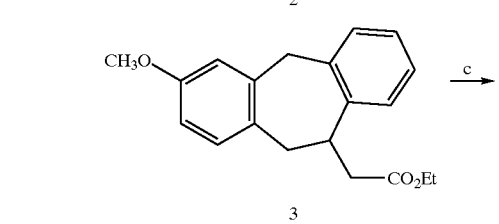

3

-continued

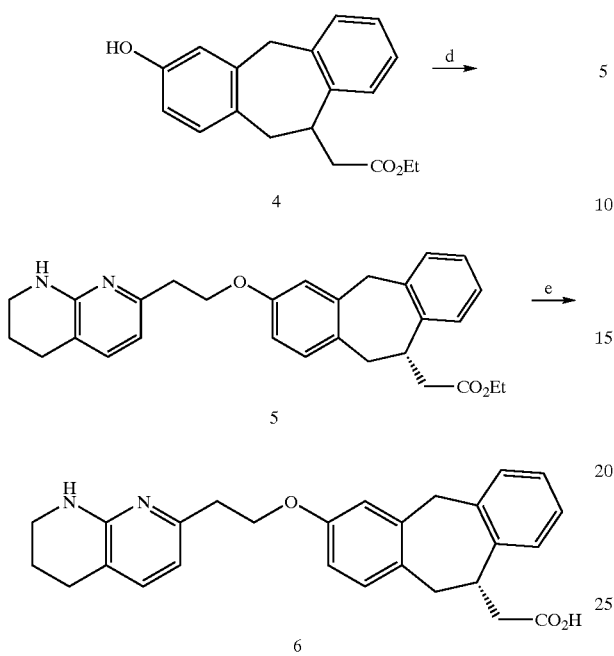

(a) EtOAc/LiHMDS, THF; (b) H$_2$, 10% Pd/C, conc. HCl, AcOH; (c) EtSH, AlCl$_3$, CH$_2$Cl$_2$; (d) 2-(5,6,7,8-tetrahydro-1,8-naphthyridin-2-yl)-1-ethanol, diisopropyl azodicarboxylate, (Ph)$_3$P; (e) 1.0 N LiOH, EtOH; HCl.

Scheme III details the preparation of a formula (I) compound. Reaction of III-1 (which is a Scheme I-3 compound) in an aldol-type reaction with the enolate of ethyl acetate, which can be generated from ethyl acetate on exposure to an appropriate amide base, for instance lithium diisopropylamide (LDA) or lithium bis(trimethylsilyl)amide (LiHMDS), gives III-2. Frequently. THF is the solvent of choice for an aldol reaction, although THF in the presence of various additives, for instance HMPA or TMEDA, is often used. Reduction of III-2 to give III-3 (which is a Scheme II-6 compound) can be accomplished by hydrogenolysis over an appropriate catalyst, for example palladium metal on activated carbon. (Pd/C), in an appropriate solvent, such as acetic acid, in the presence of a mineral acid such as HCl. Alternatively, this reduction can be accomplished by treatment of III-2 with triethylsilane in the presence of boron trifluoride etherate by the general method of Orfanopoulos and Smonou (*Synth. Commun.* 1988, 833). Removal of the methyl ether of III-3 to give III-4 can be accomplished with BBr$_3$ in an inert solvent, for example CH$_2$Cl$_2$, or by reaction with ethanethiol and AlCl$_3$ in an inert solvent, preferably CH$_2$Cl$_2$. Other useful methods for removal of a methyl ether are described in Greene, "Protective Groups in Organic Synthesis" (published by John Wiley and Sons). Compound 4 of Scheme 3 (III-4) is reacted with 2-(5,6,7,8-tetrahydro-1,8-naphthyridin-2-yl)-1-ethanol to afford III-5. The reaction is mediated by the complex formed between diisopropyl azodicarboxylate and triphenylphosphine, and is conducted in an aprotic solvent, for instance THF, CH$_2$Cl$_2$, or DMF. The ethyl ester of III-5 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid III-6. Alternatively, the intermediate carboxylate salt can be isolated, if desired, or a carboxylate salt of the free carboxylic acid can be prepared by methods well-known to those of skill in the art.

Scheme IV

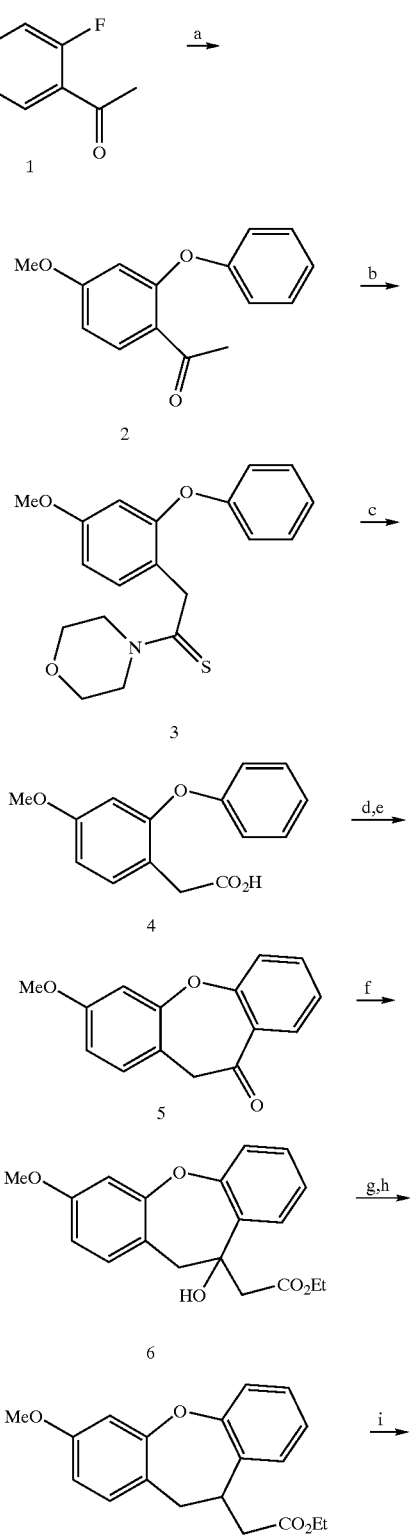

-continued

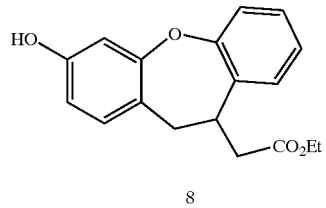

8

(a) PhOH, Cu, $K_2CO_3$; (b) sulfur, morpholine; (c) KOH, $H_2O$, i-PrOH; (d) $SOCl_2$, benzene; (e) $AlCl_3$, $CH_2Cl_2$; (f) EtOAc, $LiN(TMS)_2$, TMEDA, THF; (g) $Et_3SiH$, $BF_3 \cdot OEt_2$, $CH_2Cl_2$; (h) $H_2$, Pd/C, EtOH; (i) $BBr_3$, $CH_2Cl_2$.

Commercially available 2-fluoro-4-methoxyacetophenone (IV-1) reacts with an alcohol, for example phenol, in the presence of copper metal and a suitable base, for instance $K_2CO_3$, to afford the diaryl ether IV-2. On treatment with sulfur and an appropriate primary or secondary amine, preferably morpholine, according to the general method of Harris (*J. Med. Chem.* 1982, 25, 855), IV-2 is converted to IV-3 in a classical Willgerodt-Kindler reaction. The thioamide thus obtained is hydrolyzed to the corresponding carboxylic acid IV-4 by reaction with an alkali metal hydroxide, suitably KOH, in an aqueous alcoholic solvent, such as aqueous MeOH, EtOH, or i-PrOH. Carboxylic acid IV-4 is converted to the corresponding acid chloride by reaction with either $SOCl_2$ or oxalyl chloride according to conditions well-known to those of skill in the art. Treatment of this acid chloride with an appropriate Friedel-Crafts catalyst, such as $AlCl_3$ or $SnCl_4$, in an inert solvent, such as $CH_2Cl_2$ or $CS_2$, provides the cyclic ketone IV-5. Alternatively, acid IV-4 can be converted directly to ketone IV-5 under acidic conditions, for example with polyphosphoric acid. Reaction of IV-5 in an aldol—type reaction with the enolate of ethyl acetate, which can be generated from ethyl acetate on exposure to an appropriate amide base, for instance lithium diisopropylamide (LDA) or lithium bis(trimethylsilyl)amide (LiHMDS), gives IV-6. Frequently, THF is the solvent of choice for an aldol reaction, although THF in the presence of various additives, for instance HMPA or TMEDA, is often used. Reduction of IV-6 to give IV-7 can be accomplished by treatment of IV-6 with triethylsilane in the presence of boron trifluoride etherate by the general method of Orphanopoulos and Smonu (*Synth. Commun.* 1988, 833). Any olefinic by-products that result from elimination of the alcohol are reduced by hydrogenation over an appropriate catalyst, for example palladium metal on activated carbon (Pd/C), in an appropriate solvent, such as MeOH or EtOH. Alternatively, the reduction of IV-6 to give IV-7 can be accomplished by hydrogenolysis in the presence of a mineral acid such as HCl. Typically, this reaction is catalyzed by Pd/C, and is optimally conducted in acetic acid. Removal of the methyl ether of IV-7 to give IV-8 can be accomplished with $BBr_3$ in an inert solvent, for example $CH_2Cl_2$, or by reaction with ethanethiol and $AlCl_3$ in an inert solvent, preferably $CH_2Cl_2$. Other useful methods for removal of a methyl ether are described in Greene, "Protective Groups in Organic Synthesis" (published by John Wiley and Sons). IV-8 is subsequently converted to formula (I) compound following the procedure outlined in Scheme III.

Acid addition salts of the compound are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compound form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compound of formula (I) may be used in the manufacture of a medicament. Pharmaceutical compositions of the compound of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compound may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compound of this invention may also be combined with excipients such as cocoa butter, glycerin, gelatin or polyethylene glycols and molded into a suppository.

The compound described herein are antagonists of the vitronectin receptor, and are useful for treating diseases wherein the underlying pathology is attributable to ligand or cell which interacts with the vitronectin receptor. For instance, these compound are useful for the treatment of diseases wherein loss of the bone matrix creates pathology. Thus, the instant compound are useful for the treatment of ostoeporosis, hyperparathyroidism, Paget's disease, hypercalcemia of malignancy, osteolytic lesions produced by bone metastasis, bone loss due to immobilization or sex hormone deficiency. The compound of this invention are also believed to have utility as antitumor, anti-angiogenic, antiinflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compound are administered one to four times daily at a level to achieve a total daily dose of about 0.4 to about 400 mg/kg/day. The precise level and method by which the compound are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of formula (I) and other inhibitors of bone resorption, such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of formula (I) and an antineoplastic agent. Compound of the camptothecin analog class, such as topotecan, irinotecan and 9-aminocamptothecin, and platinum coordination complexes, such as cisplatin, ormaplatin and tetraplatin, are well known groups of antineoplastic agents. Compound of the camptothecin analog class are described in U.S. Pat. Nos. 5,004,758, 4,604,463, 4,473,692, 4,545,880, 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med. Chem.*, 1980, 23, 554, Wani, et al., *J. Med. Chem*, 1987, 30, 1774, and Nitta, et al., *Proc. 14th International Congr. Chemotherapy.*, 1985, *Anticancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S. Pat. Nos. 5,562,925 and 4,310,515, the entire disclosure of each which is hereby incorporated by reference.

In the method of inhibiting tumor growth which comprises administering stepwise or in physical combination a compound of formula (I) and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter (mg/m$^2$) of body surface area per course of treatment. Infusions of the platinum coordiation compound may be given one to two times weekly, and the weekly treatments may be repeated several times. Using a compound of the camptothecin analog class in a parenteral administration, the course of therapy generally employed is from about 0.1 to about 300.0 mg/m$^2$ of body surface area per day for about five consecutive days. Most preferably, the course of therapy employed for topotecan is from about 1.0 to about 2.0 mg/m$^2$ of body surface area per day for about five consecutive days. Preferably, the course of therapy is repeated at least once at about a seven day to about a twenty-eight day interval.

The pharmaceutical composition may be formulated with both the compound of formula (I) and the antineoplastic agent in the same container, but formualtion in different containers is preferred. When both agents are provided in solution form, they can be contained in an infusion/injection system for simultaneous administration or in a tandem arrangement.

For convenient administration of the compound of formula (I) and the antineoplastic agent at the same or different times, a kit is prepared, comprising, in a single container, such as a box, carton or other container, individual bottles, bags, vials or other containers each having an effective amount of the compound of formula (I) for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of formula (I) may be in an i.v. injectable form, or infusion bag linked in series, via tubing, to the antineoplastic agent in a second infusion bag. Using such a system, a patient can receive an initial bolus-type injection or infusion of the compound of formula (I) followed by an infusion of the antineoplastic agent.

The compound may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM CaCl$_2$ and 1% octylglucoside) was diluted with buffer T containing 1 mM CaCl$_2$, 1 mM MnCl$_2$, 1 mM MgCl2 (buffer A) and 0.05% NaN$_3$, and then immediately added to 96-well ELISA plates (Corning, New York, N.Y.) at 0.1 mL per well. 0.1–0.2 $\mu$g of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compound were dissolved in 100% DMSO to give a 2 mM stock solution, which was diluted with binding buffer (15 mM Tris-HCl (pH 7.4), 100 mM NaCl, 1 mM CaCl$_2$, 1 mM MnCl$_2$, 1 mM MgCl$_2$) to a final compound concentration of 100 $\mu$M. This solution is then diluted to the required final compound concentration. Various concentrations of unlabeled antagonists (0.001–100 $\mu$M) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 $\mu$M SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to the equation: $K_i=IC_{50}/(1+L/K_d)$, where L and K$_d$ were the concentration and the dissociation constant of [$^3$H]-SK&F-107260, respectively.

The compound of the present invention inhibits vitronectin binding to SK&F 107260 at a K$_i$ of about 1.7 nanomolar.

Compound of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of $2.5–5.0\times10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% CO$_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1-34 peptide (hPTH1-34, dose 1.25 ug/kg/h in saline/0.1% bovine serum albumin, Bachem, Ca) or a mixture of hPTH1-34 and test material, by continuous intravenous infusion via the venous catheter using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitve ELISA.

Assay 1 (Using Laser Confocal Microscopy)

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control (IgG$_{2a}$ diluted to 100 ug/ml). The samples are incubated at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh medium containing the compound treatment or control samples. The samples are incubated at 37° C. for 48 hours.

Tartrate Resistant Acid Phosphatase (TRAP) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylfornamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/ purple precipitate) are enumerated by bright-field microscopy and are then removed from the surface of the dentine by sonication.

Pit volumes are determined using the Nikon/Lasertec ILM21W confocal microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method desribed above in Assay 1, the compound are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His- Asp-Gly-Gly-Arg) that is present in the carboxy-terminal telopeptide of the a1-chain of type I collagen. The results are expressed as % inhibition of resorption compared to a vehicle control.

Human Osteoclast Adhesion Assay

The human osteoclasts are enriched and prepared for compound screening as described above in the inital 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts, This wash process is repeated×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tattrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay
Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the $\alpha_v$ subunit and a 2.4 kb XbaI-XhoI fragment of the $\beta_3$ subunit were inserted into the EcoRI-EcoRV cloning sites of the pCDN vector (Aiyar et al., 1994 ) which contains a CMV promoter and a G418 selectable marker by blunt end ligation. For stable expression, 80×10$^6$ HEK 293 cells were electrotransformed with $\alpha_v+\beta_3$ constructs (20 μg DNA of each subunit) using a Gene Pulser (Hensley et al., 1994 ) and plated in 100 mm plates (5×10$^5$ cells/plate). After 48 hr, the growth medium was supplemented with 450 μg/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 μg/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0.1% BSA at a density of 0.5×10$^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water. The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-Phase $\alpha_v\beta_5$ Binding Assay

The vitronectin receptor $\alpha_v\beta_5$ was purified from human placenta. Receptor preparation was diluted with 50 mM Tris-HCl, pH 7.5, 100 mM NaCl, 1 mM CaCl$_2$, 1 mM MnCl$_2$, 1 mM MgCl$_2$ (buffer A) and was immediately added to 96-well ELISA plates at 0.1 ml per well. 0.1–0.2 μg of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer for 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 μM) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion. The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 μM SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to Cheng and Prusoff equation: $K_i=IC_{50}/(1+L/K_d)$, where L and K$_d$ were the concentration and the dissociation constant of [$^3$H]-SK&F-107260, respectively.

Inhibition of RGD-mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 40° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl$_2$ (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIB-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [$^3$H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [$^3$H]-SK&F-107260 used in the competitive binding assay (4.5 nM), and Kd is the dissociation constant of [$^3$H]-SK&F-107260 which is 4.5 nM as determined by Scatchard analysis.

The efficacy of the compound of formula (I) alone or in combination with an antineoplastic agent may be determined using several transplantable mouse tumor models. See U.S. Pat. Nos. 5,004,758 and 5,633,016 for details of these models The examples which follow are intended in no way to limit the scope of this invention, but are provided to illustrate how to make and use the compound of this invention. Many other embodiments will be readily apparent to those skilled in the art.

EXAMPLES

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical and preparative HPLC were carried out on Beckman chromatographs. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Preparation 1

Preparation of 2-(5,6,7,8-tetrahydro-1,8-naphthyridin-2-yl)-1-ethanol a) 2-Methyl-8-(tert-butoxycarbonyl)-5,6,7,8-tetrahydro-1,8-naphthyridine A mixture of 2-methyl-1,8-naphthyridine (*J. Chem. Soc.* (C) 1966, 315; 5.13 g, 35.58 mmole), 10% Pd/C (1.14 g, 1.07 mmole), and absolute EtOH (70 mL) was deoxygenated through three evacuation/H$_2$ purge cycles, then was stirred briskly under a balloon of H$_2$. After 18.5 hr, the mixture was filtered through celite®, and the filter pad was washed sequentially with absolute EtOH and EtOAc. The filtrate was concentrated to dryness, and the residue was reconcentrated from EtOAc to leave an off-white solid (5.25 g).

A solution of the above material (5.25 g), di-tert-butyl dicarbonate (15.53 g, 71.16 mmole), and CH$_2$Cl$_2$ (10 mL) was concentrated on the rotavap to remove the solvent, and the oily residue was heated under N$_2$ in an oil bath set at 55–60° C. After 45 hr, the reaction was cooled to RT, and the residue was flash chromatographed on silica gel (40% EtOAc/hexanes). The title compound (4.90 g, 55%) was obtained as a light yellow solid: $^1$H NMR (300 MHz, CDCl$_3$) δ7.27 (d, J=7.6 Hz, 1H), 6.81 (d, 7.6 Hz, 1H), 3.69 –3.79 (m, 2H), 2.65–2.75 (m, 2H), 2.48 (s, 3H), 1.83–1.98 (m, 2H), 1.52 (s, 9H), MS (ES) m/e 249 (M+H)$^+$.

b) Ethyl [8-(tert-butoxycarbonyl)-5,6,7,8-tetrahydro-1,8-naphthyridin-2-yl]acetate To a solution of diisopropylamine (7.24 mL, 55.3 mmole) in dry TBF (50 mL) was added n-BuLi (2.5 M in hexanes, 22 mL, 55.3 mmole) dropwise at 0° C. After 15 min, this solution was added dropwise to a solution of 2-methyl-8-(tert-butoxycarbonyl)-5,6,7,8-tetrahydro-1,8-naphthyridine (4.9 g, 19.7 mmole) and diethylcarbonate (8.86 mL, 73.0 mmole) in dry THF (50 mL) at −78° C. After 30 min, the mixture was quenched with saturated NH$_4$Cl (100 mL), warmed to RT, and extracted with EtOAc (3×200 mL). The combined organic extracts were dried over MgSO$_4$, filtered, and concentrated under reduced pressure. The residue was chromatographed on silica gel (40% EtOAc/hexanes) to give the title compound (5.72 g, 91%) as a light yellow oil: MS (ES) m/e 321 (M+H)$^+$.

c) 2-(5,6,7,8-Tetrahydro-1,8-naphthyridin-2-yl)-1-ethanol

To a solution of ethyl [8-(tert-butoxycarbonyl)-5,6,7,8-tetrahydro-1,8-naphthyridin-2-yl]acetate (5.72 g, 17.85 mmole) in dry THF (80 mL) at RT was added LiBH$_4$ (2.0 M in THF, 10.7 mL, 21.42 mmole), and the resulting mixture was heated to reflux. After 18 hr, the mixture was cooled to 0° C. and carefully quenched with H$_2$O (100 mL). After 10 min, the mixture was extracted with EtOAc (3×100 mL). The combined organic extracts were dried over MgSO$_4$, filtered, and concentrated under reduced pressure.

The above residue (4.9 g) was dissolved in CH$_2$Cl$_2$ (10 mL). To this was added 4 N HCl in dioxane (20 mL) all at once at RT. After 4, the mixture was concentrated under reduced pressure. The residue was taken up in a 1:1 mixture of 1.0 N NaOH and saturated NaCl (100 mL) and extracted with CH$_2$Cl$_2$ (3×100 mL). The combined organic extracts were dried over MgSO$_4$, filtered, and concentrated under reduced pressure. The residue was chromatographed on silica gel (10% MeOH in 1:1 EtOAc/CHCl$_3$) to give the title compound (2.09 g, 66%) as a yellow solid: MS (ES) m/e 179 (M+H)$^+$.

Preparation 2

Preparation of ethyl (±)-10,11-dihydro-3-hydroxy-5H-dibenzo[a,d]cycloheptene-10-acetate a) 6-Methoxy-1-phenylindene A solution of 3.0 M phenylmagnesium bromide in $Et_2O$ (680 mL, 2.04 mole) under argon at ambient temperature was diluted with $Et_2O$ (700 mL) with stirring, and a solution of 6-methoxy-1-indanone (277 g, 1.71 mole) in THF (1400 mL) was added dropwise over 1 hr. The reaction mixture was stirred for 2 h at ambient temperature and then was poured with stirring into saturated $NH_4Cl$ (2.8 L). $H_2O$ (1.4 L) was added, and the organic phase separated. The aqueous phase was extracted with $Et_2O$ (2×1 L), and the combined organic extracts were concentrated to give crude 6-methoxy-1-phenyl-1-indanol (445 g) as a brown oil. This oil was dissolved in toluene (2.5 L), and p-toluenesulfonic acid monohydrate (12.3 g, 0.065 mole) was added. The solution was stirred and heated at reflux for 16 hr using a Dean-Stark trap with a condenser. $H_2O$ collection was minimal after 2 h and totaled 28 mL. The solution was cooled and extracted sequentially with 5% aqueous $Na_2CO_3$ (1 L) and $H_2O$ (2×1 L). The organic layer was concentrated to give a dark brown oil (400 g). This oil was distilled under vacuum to give the title compound (298.2 g, 79%) as a yellow oil: bp 152–190° C./2.0 Torr; TLC (10% EtOAc/hexanes) $R_f$ 0.75.

b) 2-Benzoyl-4-methoxyphenylacetic Acid

Acetone (4.2 L) was chilled to 10° C., and a solution of 6-methoxy-1-phenylindene (271 g, 1.22 mole) in acetone (1.8 L) was added over 1.5 hr concurrently with Jones reagent (1.8 L, prepared from $CrO_3$ (470 g, 4.70 mole), $H_2O$ (1 L), and conc $H_2SO_4$ (405 mL)). 4% Aqueous $OsO_4$ (153 mL) was added to the resulting mixture in two portions, one at the onset of addition and the second at the mid-point of the addition, maintaining the temperature of the reaction mixture below 15° C. Following the addition, the reaction mixture was warmed to 22° C. and stirred for 1.5 h, during which time a mild exotherm increased the temperature to 28° C. The reaction mixture was then cooled to below 20° C. and isopropanol (1 L) was added, dropwise initially and rapidly after the initial exotherm diminished. Stirring became difficult during this phase. The temperature reached 32° C. during the isopropanol addition. $H_2O$ (2 L) was added and the mixture was transferred to a separatory funnel. Additional $H_2O$ was added to dissolve the precipitated chromous acid, and the mixture was extracted with $CH_2Cl_2$ (2 L). The organic (upper) layer was separated and the aqueous phase was extracted with $CH_2Cl_2$ (2×1 L). The combined $CH_2Cl_2$ extracts were washed sequentially with $H_2O$ (2 L) and saturated brine (2 L), and then were concentrated to give a moist gray solid (416 g). This was triturated with a mixture of acetone and EtOAc and filtered and dried to give the title compound (225.4 g, 71%) as an off-white solid: mp 158–159° C.

c) 2-Benzyl-4-methoxyphenylacetic Acid

2-Benzoyl-4-methoxyphenylacetic acid (215.5 g, 0.80 mole) was divided into two equal portions, and each was dissolved in glacial AcOH (1.5 L) in a 2.5 L pressure bottle. 5% Pd/C (10 g, 0.0048 mole) was added to each, and each mixture was shaken at ambient temperature under hydrogen on a Parr apparatus. After 2.5 hr, the mixtures were filtered to remove the catalyst, and the filter pads were washed with EtOAc. The combined filtrates were concentrated to give the title compound (215 g, quantitative) as a heavy yellow oil which crystallized on standing: $^1$H NMR (250 MHz, $CDCl_3$) δ7.05–7.35 (m, 6H), 6.77 (dd, J=8.3, 2.7 Hz, 1H), 6.71 (d, J=2.7 Hz, 1H), 4.00 (s, 2H), 3.76 (s, 3H), 3.54 (s, 2H).

d) 10,11-Dihydro-3-methoxy-5H-dibenzo[a,d]cyclohepten-10one

A solution of 2-benzyl-4methoxyphenylacetic acid (215 g of crude material that contained 204.6 g (0.80 mole) of pure material) in $CH_2Cl_2$ (1 L) was stirred under argon at ambient temperature, and DMF (1 mL) was added, followed by oxalyl chloride (400 mL, 4.59 mole). The oxalyl chloride was added over 1 hr, dropwise initially to control the vigorous gas evolution. The solution was stirred for 16 h at ambient temperature and then was concentrated to give the crude acid chloride (207.7 g, 0.756 mol, 95%) as a yellow liquid. This liquid was dissolved in $CH_2Cl_2$ to a total volume of 500 mL, and the solution and $AlCl_3$ (100.8 g, 0.756 mol) were added concurrently over 1 hr to $CH_2Cl_2$ (3.7 L) with stirring under argon at ambient temperature. The temperature was 28° C. at the completion of the addition. The reaction mixture was stirred for 16 h at ambient temperature, during which time a solid precipitated. $H_2O$ (1 L) was added, initially dropwise, over a period of 30 min. The mixture was then separated and the organic phase was washed sequentially with $H_2O$ (1 L) and 5% aqueous $NaHCO_3$ (1 L). The $CH_2Cl_2$ solution was then concentrated to give a yellow solid (175.3 g). Recrystallization from EtOAc/hexane gave the title compound (128 g, 71%): mp 107–109° C.

e) Ethyl (±)-10,11-dihydro-10-hydroxy-3-methoxy-5H-dibenzo[a,d]cycloheptene-10-acetate A 1.0 M solution of lithium bis(trimethylsilyl)amide in hexanes (1282 mL, 1.282 mole) was added to THF (4.0 L) at −70° C. under argon, then EtOAc (146 mL, 1.49 mole) was added dropwise over 20 min. The reaction mixture was allowed to stir for 15 min, then N,N,N',N'-etramethylethlylenediamine (378 mL, 2.5 mole) was added over 20 min. The reaction mixture was stirred for 10 min, then a solution of 10,11-dihydro-3-methoxy-5H-dibenzo[a,d]cyclohepten-10-one (119.2 g, 0.50 mol) in anhydrous THF (1.26 L) was added dropwise over 40 min. The temperature was maintained below −65° C. during all of these additions. The reaction mixture was stirred for 20 min at −65 to −70° C. and then was poured into saturated aqueous $NH_4Cl$ (6.2 L) with vigorous stirring. The organic layer was separated and the aqueous phase was extracted with EtOAc (2×1 L). The combined organic extracts were washed with $H_2O$ (2×1 L) and then were concentrated to give a light brown oil (175 g). Thin-layer chromatography (20% EtOAc/hexanes) showed $R_f$ 0.5 major (desired product) and $R_f$ 0.7 minor (recovered ketone). The crude product was chromatographed on silica gel (2 kg, 10% EtOAc/hexanes) to afford the title compound (101 g, 61%) as a yellow oil: $^1$H NMR (250 MHz, $CDCl_3$) δ7.63 (d, J=7.7 Hz, 1H), 7.00–7.30 (m, 4H), 6.80 (d, J=2.6 Hz, 1H), 6.69 (dd, J=8.2, 2.6 Hz, 1H), 3.95–4.35 (m, 2H), 4.07 (s, 2H), 3.76 (s, 3H), 3.68 (s, 1H), 3.64 (d, J=14.2 Hz, 1H), 3.35 (d, J=14.2 Hz, 1H), 2.79 (d, J=16.0 Hz, 1H), 2.66 (d, J=16.0 Hz, 1H), 1.22 (t, J=7.2 Hz, 3H).

f) Ethyl (±)-10,11-dihydro-3-methoxy-5H-dibenzo[a,d]cycloheptene-10-acetate

Ethyl (±)-10,11-dihydro-10hydroxy-3-methoxy-5H-dibenzo[a,d]cycloheptene-10-acetate (101 g, 0.31 mole) was dissolved in glacial acetic acid (1.8 L) and 12 N HCl (28.5 mL, 0.34 mole) was added. The mixture was placed in a 2.5 L pressure both containing 5% Pd/C (20 g, 0.0094 mole), and the resulting mixture was shaken at 35° C. under hydrogen on a Parr hydrogenation apparatus equipped with a jacket heater. After 18 hr, the reaction was cooled to ambient temperature, and the catalyst was removed by filtration. The filtrate was concentrated to give a light yellow oil (85.1 g). This was chromatographed on silica gel (2 kg, step-gradient with 5% to 10% EtOAc/hexanes) to afford the title compound (69.1 g, 72%) as an oil: $^1$H NMR (250 MHz, $CDCl_3$ δ7.05–7.22 (m, 4H), 7.01 (d, J=8.2 Hz, 1H), 6.76 (d, J=2.7 Hz, 1H), 6.67 (dd, J=8.2, 2.7 Hz, 1H), 4.30 (d, J=15.0 Hz, 1H), 4.11–4.25 (m, 2H), 3.85 (d, J=15.0 Hz, 1H), 3.70–3.90 (m, 1H), 3.77 (s, 3H), 3.31 (dd, J=15.0, 4.1 Hz, 1H), 2.93 (dd, J=15.0, 9.2 Hz, 1H), 2.64 (dd, J=15.6, 5.0 Hz, 1H), 2.52 (dd, J=15.6, 9.3 Hz, 1H), 1.27 (t, J=7.1 Hz, 3H).

g) Ethyl (±)-10,11-dihydro-3-hydroxy-5H-dibenzo[a,d]cycloheptene-10-acetate

A solution of ethyl (±)-10,11-dihydro-3-methoxy-5H-dibenzo[a,d]cycloheptene-10-acetate (8.5 g, 0.027 mole) in $CH_2Cl_2$ (150 mL) was chilled to $-10°$ C. with stirring under argon. Ethanethiol (10.7 mL, 0.144 mole) was added, followed by $AlCl_3$ (20.6 g, 0.154 mole) in two portions over 15 min. An exotherm increased the temperature to $0°$ C. following the additions, and the temperature was then increased to $25°$ C. using a water bath. The reaction mixture was stirred at 25 to $30°$ C. for 2.25 hr, at which point it was poured into ice-$H_2O$. The organic layer was separated, methanol (100 mL) was added, and the mixture was extracted with $CH_2Cl_2$ (2×50 mL). The combined $CH_2Cl_2$ extracts were washed with $H_2O$ (250 mL) and then were concentrated to give a viscous oil (8.6 g). This was taken up in $Et_2O$ (150 mL) and the ether was boiled off while replacing it with hexane. The desired phenol first separated as an oil which crystallized on stirring at ambient temperature. Two crops of solid were collected to afford the title compound (7.1 g, 89%): mp 110–112° C.

Preparation 3

HPLC Separation of the Enantiomers of ethyl (±)-10,11-dihydro-3-hydroxy-5H-dibenzo[a,d]cycloheptene-10-acetate a) Ethyl (R)-(+)-10,11-dihydro-3-hydroxy-5H-dibenzo[a,d]cycloheptene-10-acetate and ethyl (S)-(-)-10,11 -dihydro-3-hydroxy-5-dibenzo[a,d]cycloheptene-10-acetate Ethyl (±)-10,11-dihydro-3-hydroxy-5H-dibenzo[a,d]cycloheptene-10-acetate was resolved into its enantiomers using the following conditions: Daicel Chiralcel OJ® column (21.2×250 mm), 20% ethanol in hexane mobile phase, 15 mL/min flow rate, uv detection at 254 nm, 140 mg injection; $t_R$ for ethyl (S)-(-)-10,11-dihydro-3-hydroxy-5-dibenzo[a,d]cyclohexene-10-acetate=10.4 min.; $t_R$ for ethyl (R)-(+)-10,11-dihydro-3-hydroxy-5H-dibenzo[a,d]cyclohexene-10-acetate=13.1 min.

Preparation 4

Preparation of 10,11-Dihydro-3-methoxy-5H-dibenzo[a,d]cyclohepten-10-one a) 2-Benzyl-4-methoxyphenylacetic Acid A solution of 2-benzoyl-4-methoxyphenylacetic acid (13.0 g, 0.048 mol), prepared by the method of *J. Med. Chem.* 1981, 24, 998, in glacial acetic acid (600 mL) was treated under argon with 4.3 g. of 10% Pd/C and hydrogenated at 50 psi for 17 hours. The mixture was filtered using celite® and the filtrate was concentrated and reconcentrated from toluene and methylene chloride to give 14.2 of the title compound: $^1$H NMR (400 MHz, $CDCl_3$) δ3.52 (s, 2H), 3.75 (s, 3H), 4.0 (s, 3H), 6.7 (m, 2H), 7.15 (m, 6H).

b) 10,11-Dihydro-3-methoxy-5H-dibenzo[a,d]cyclohepten-10-one

A solution of 2-benzyl-4-methoxyphenylacetic acid (14.2 g, 0.055 m) in benzene (120 mL) and thionyl chloride (28 mL) was refluxed for 1 hour and concentrated. The acid chloride was dissolved in dry methylene chloride (40 mL), and the solution was added dropwise under argon to a solution of $AlCl_3$ (14.7 g, 0.11 mol) in methylene chloride (600 mL). The reaction was stirred under an argon atmosphere for 2.5 hours at room temperature, then was quenched with ice-water (200 mL). The layers were separated, and the organic phase was washed sequentially with 10% NaOH solution, water, and dil. HCl. The resulting solution was diluted with ether (200 mL), dried over $MgSO_4$, and concentrated. The solid residue was triturated with ether/hexane (1:1) and 9.35 g of the title compound was collected by filtration: Mp 105–106° C.; $^1$H NMR (400 MHz, $CDCl_3$) δ3.72 (s, 3H), 4.1 (s, 2H), 4.2 (s, 2H), 6.7 (d, 1H), 6.82 (s, 1H), 7.30 (m, 4H), 8.1 (d, 1H).

Preparation 5

Preparation of ethyl (±)-10,11-dihydro-3-methoxy-5H-dibenzo[a,d]cycloheptene-10-acetate a) Ethyl (±) 3-(3-methoxyphenyl)indeneacetate To a cold solution of 3-(3-methoxyphenyl)indene (4 g, 18 mmol), prepared by the method of *J. Med. Chem.* 1981, 24, 998, in THF (15 mL) at $0°$ C. was added dropwise a solution of $LiN(TMS)_2$ (20 mL, 1M in THF) over 5 min. The resulting solution was added dropwise to a solution of ethyl bromoacetate (3.34 g, 20 mmol) in THF (15 mL) at $-78°$ C. over 30 min. After 2.5 h, the mixture was quenched with saturated ammonium chloride solution and the layers were separated. The organic layer was dried over $MgSO_4$ and concentrated to give the crude product which was purified by column chromatography ($SiO_2$/2–4% EtOAc/hexane) to give title compound (1.1 g): $^1$H NMR (400 MHz, $CDCl_3$) δ1.30 (t, 3H), 2.50 (m, 1H), 2.85 (m, 1H), 3.85 (s, 3H), 4.0 (m, 1H), 4.20 (q, 2H), 6.6 (s, 1H), 6.9 (m, 1), 7.2 (s, 1H), 7.35 (m, 6H).

b) Ethyl (±) 3-[(3-methoxybenzoyl)]phenylsuccinate

A solution of ethyl (±) 3-(3-methoxyphenyl)indeneacetate (1.1 g, 3.6 mmol) in acetone (30 mL) was treated with 4% aqueous solution of osmium tetroxide (0.5 mL) followed by a dropwise addition of 1.2 M Jones reagent (5 mL, 6 mmol) according to the literature procedure (*J. Org. Chem.* 1993, 58, 4745). After stirring overnight at room temperature, the dark reaction mixture was quenched with isopropanol (2.5 mL), followed by sodium bisulfite (0.9 g) and water (30 mL). The product was extracted with ethyl acetate, washed with brine, dried over $MgSO_4$, and concentrated to give a solid residue. Trituration with 1:1 ether/hexane gave 0.76 g of the title compound: $^1$H NMR (400 MHz, $CDCl_3$) δ1.18 (t, 3H), 2.90 (m, 1H), 3.3 (m, 1H), 3.92 (s, 3H), 4.1 (q, 2H), 4.4 (m, 1H), 4.4 (d, 1H), 7.25 (m, 2H), 7.5 (m, 6H).

c) Ethyl (±) 3-[(3-methoxybenzyl)]phenylsuccinate

A mixture of ethyl (±) 3-[(3-methoxybenzoyl)]phenylsuccinate (0.76 g., 2.1 mmol) and 10% Pd/C (0.6 g) in glacial acetic acid (35 mL) was hydrogenated at 50 psi for 17 hours. The mixture was filtered using celite® and the filter pad was washed with acetic acid. The filtrate was concentrated and reconcentrated from toluene and methylene chloride to give 0.65 g of the title compound: $^1$H NMR (400 MHz, $CDCl_3$) δ1.20 (t, 3H), 2.20 (m, 1H), 3.0 (m, 1H), 3.74 (s, 3H), 4.1 (q, 2H), 4.18 (q, 2H), 4.4 (d, 1H), 6.2 (m, 2H), 7.22 (m, 6H).

d) Ethyl (±)-10,11-dihydro-3-methoxy-11-oxo-5-dibenzo[a,d]cycloheptene-10-acetate To a magnetically stirred solution of ethyl (±) 3-[(3-methoxybenzyl)]phenylsuccinate (0.65 g, 1.9 mmol) in dry methylene chloride (10 mL) were added DMF (0.2 mL) and oxalyl chloride (0.2 mL, 2.28 mmol). After 1.5 h, the solution was added dropwise to a suspension of aluminum chloride (0.6 g, 4.5 mmol) in dry methylene chloride (15 mL). The mixture was quenched after 2 h with ice water, the layers were separated, and the aqueous layer was extracted with methylene chloride. The combined organic layers were dried over $MgSO_4$ and concentrated. The residue was purified by column chromatography ($SiO_2$/2–4% EtOAc/hexane) to give title compound (0.3 g): $^1$H NMR (400 MHz, $CDCl_3$) δ1.28 (t, 3H), 2.88 (m, 1H), 3.55 (m, 1H), 3.84 (s, 3H), 3.88 (d, 1H), 4.18 (q, 2H), 4.85 (d, 1H), 4.95 (m, 1H), 5.8 (m, 2H), 7. 22(m, 4H), 8.1 (s, 1H).

e) Ethyl (±)-10,11-dihydro-3-methoxy-5H-dibenzo[a,d]cycloheptene-10-acetate

A mixture of ethyl (±)-10,11-dihydro-3-methoxy-11-oxo-5H-dibenzo[a,d]cycloheptene-10-acetate (0.3 g., 0.93 mmol) and 10% Pd/C (0.3 g) in glacial acetic acid (25 mL) was hydrogenated at 50 psi for 18 hours. The mixture was filtered using celite® and washed with acetic acid. The filtrate was concentrated and reconcentrated from toluene and methylene chloride to give 0.25 g of the title compound: $^1$H NMR (400 MHz, $CDCl_3$) δ1.28 (t, 3H), 2.60 (m, 2H), 2.90 (m, 1H), 3.30 (m, 1H), 3.80 (s, 3H), 3.85 (d, 1H), 4.18 (q, 2H), 4.30 (d, 1H), 6.70 (m, 2H), 7.0 (d, 1H), 7.22 (m, 4H).

The following example illustrates a method for preparing the biologically active compound of this invention from intermediate compounds such as described in the foregoing Preparations.

Example 1

Preparation of (S)-10,11-dihydro-3-[2-(5,6,7,8-tetrahydro-1,8-naphthyridin-2-yl)-1-ethoxy]-5H-dibenzo[a,d]cycloheptene-10-acetic Acid a) Ethyl (S)-10,11-dihydro-3-[2-(5,6,7,8-tetrahydro-1,8-naphthyridin-2-yl)-1-ethoxy]-5H-dibenzo[a,d]cycloheptene-10-acetate To a solution of ethyl (S)-10,11 -dihydro-3-hydroxy-5H-dibenzo[a,d]cycloheptene-10-acetate (200 mg, 0.67 mmole), 2-(5,6,7,8-tetrahydro-1,8-naphthyridin-2-yl)-1-ethanol (241 mg, 1.35 mmole), and $PPh_3$ (354 mg, 1.35 mmole) in dry THF (5 mL) was added diisopropyl azodicarboxylate (0.27 mL, 1.35 mmole) at 0° C. The mixture was allowed to warm to RT as the bath warmed. After 18 hr, the mixture was concentrated under reduced pressure. The residue was chromatographed on silica gel (1:4.5 hexanes/$Et_2O$) to give the title compound (94 mg, 31%) as a clear oil: MS (ES) m/e 457 (M+H)$^+$.

b) (S)-10,11-Dihydro-3-[2-(5,6,7,8-tetrahydro-1,8-naphthyridin-2-yl)-1-ethoxy]-5H-dibenzo[a,d]cycloheptene-10-acetic acid To a solution of ethyl (S)-10,11-dihydro-3-[2-(5,6,7,8-tetrahydro-1,8-naphthyridin-2-yl)-1-ethoxy]-5H-dibenzo[a,d]cycloheptene-10-acetate (131 mg, 0.29 mmole) in THF/$H_2O$ (2 mL) was added 1.0 N LiOH (0.43 mL, 0.43 mmole), and the mixture was heated to 50° C. After 18 hr, the mixture was cooled to RT and washed with $Et_2O$ (2×2 mL). The aqueous layer was acidified to pH 6 using 10% HCl. The resulting milky solution was passed through a C-18 bond-elute column (gradient elution: $H_2O$, then 20% $CH_3CN$/$H_2O$, then $CHCl_3$ as eluent). Fractions containing the product were concentrated under reduced pressure to give the title compound (30 mg, 24%) as a white powder: MS (ES) m/e 429 (M+H)$^+$. Anal. Calcd for $C_{27}H_{28}N_2O_3$·0.95 HCl: C, 70.02; H, 6.30; N, 6.05. Found: C, 70.01; H, 6.33; N, 5.71.

Example 2
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 3
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 4
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

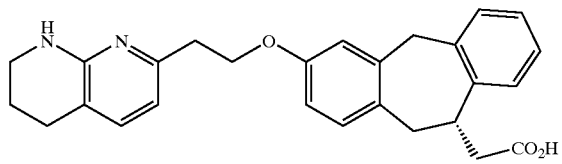

or a pharmaceutically acceptable salt thereof.

2. A pharmaceutical composition which comprises a compound according to claim 1 and a pharmaceutically acceptable carrier.

3. A pharmaceutical composition which comprises a compound according to claim 1, an antineoplastic agent and a pharmaceutically acceptable carrier.

4. The pharmaceutical composition according to claim 3 wherein the antineoplastic agent is topotecan.

5. The pharmaceutical composition according to claim 3 wherein the antineoplastic agent is cisplatin.

6. A method of treating a disease state in which antagonism of the $\alpha_v\beta_3$ receptor is indicated which comprises administering to a subject in need thereof a compound according to claim 1.

7. A method of treating a disease state in which antagonism of the $\alpha_v\beta_5$ receptor is indicated which comprises administering to a subject in need thereof a compound according to claim 1.

8. A method of treating osteoporosis which comprises administering to a subject in need thereof a compound according to claim 1.

9. A method for inhibiting angiogenesis which comprises administering to a subject in need thereof a compound according to claim 1.

10. A method for inhibiting tumor growth or tumor metastasis which comprises administering to a subject in need thereof a compound according to claim 1.

11. A method of treating atherosclerosis or restenosis which comprises administering to a subject in need thereof a compound according to claim 1.

12. A method of treating inflammation which comprises administering to a subject in need thereof a compound according to claim 1.

13. A method of inhibiting tumor growth which comprises administering stepwise or in physical combination a compound according to claim 1 and an antineoplastic agent.

14. The method according to claim 13 wherein the antineoplastic agent is topotecan.

15. The method according to claim 13 wherein the antineoplastic agent is cisplatin.

16. A compound according to formula (II):

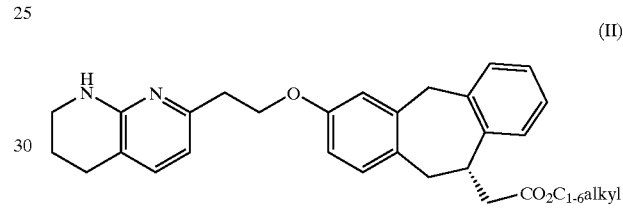

or a pharmaceutically acceptable salt thereof.

17. A process for preparing a compound of the formula (I) as defined in claim 1, which process comprises reacting a compound of formula (III):

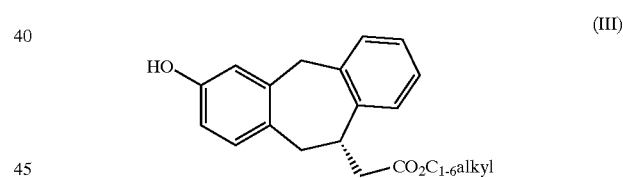

with 2-(5,6,7,8-tetrahydro-1,8-naphthyridin-2-yl)-1-ethanol in a reaction mediated by the complex formed between diisopropyl azodicarboxylate and triphenylphosphine, followed by ester hydolysis using aqueous base.

* * * * *

SEQUENCE LISTING

<160> NUMBER OF SEQ ID NOS: 2

<210> SEQ ID NO 1
<211> LENGTH: 7
<212> TYPE: DNA
<213> ORGANISM: Homo sapien

<400> SEQUENCE: 1 arggyas

```
<210> SEQ ID NO 2
<211> LENGTH: 17
<212> TYPE: DNA
<213> ORGANISM: Homo Sapien

<400> SEQUENCE: 2
guysaahsas gygyarg                                                17
```